United States Patent
Indriksons et al.

[11] Patent Number: 5,770,086
[45] Date of Patent: Jun. 23, 1998

[54] METHODS AND APPARATUS USING HYDROGELS

[75] Inventors: Andris Indriksons, Zionsville; Patricia C. Andrews, Camby, both of Ind.

[73] Assignee: Eureka! Science Corp., Indianapolis, Ind.

[21] Appl. No.: 591,139

[22] Filed: Jan. 25, 1996

[51] Int. Cl.$^6$ .......................... B01D 11/00; B01D 61/40; G01N 33/558

[52] U.S. Cl. .................. 210/643; 210/321.6; 210/644; 422/101; 422/102; 435/7.1; 436/514; 436/518; 436/824

[58] Field of Search ................ 210/321.87, 650, 210/642, 644, 321.6, 645, 502.1, 490, 500.35, 635, 643; 436/514, 515, 535, 824, 517, 518; 422/101, 102; 435/7.1

[56] References Cited

U.S. PATENT DOCUMENTS

| | | |
|---|---|---|
| 3,062,737 | 11/1962 | Azorlosa et al. ............... 210/644 |
| 3,485,751 | 12/1969 | Herrmann et al. ............. 210/645 X |
| 3,645,687 | 2/1972 | Nerenberg . |
| 3,669,103 | 6/1972 | Harper et al. . |
| 3,843,324 | 10/1974 | Edelman et al. . |
| 3,966,897 | 6/1976 | Renn et al. . |
| 4,039,652 | 8/1977 | Adams et al. . |
| 4,061,468 | 12/1977 | Lange et al. . |
| 4,094,647 | 6/1978 | Deutsch et al. . |
| 4,125,372 | 11/1978 | Kawai et al. . |
| 4,138,474 | 2/1979 | Updike . |
| 4,153,675 | 5/1979 | Kleinerman . |
| 4,168,146 | 9/1979 | Grubb et al. . |
| 4,180,383 | 12/1979 | Johnson . |
| 4,193,983 | 3/1980 | Ullman et al. . |
| 4,235,601 | 11/1980 | Deutsch et al. . |
| 4,376,110 | 3/1983 | David et al. . |
| 4,424,279 | 1/1984 | Bohn et al. . |
| 4,427,769 | 1/1984 | Adlercreutz et al. . |
| 4,486,530 | 12/1984 | David et al. . |
| 4,524,186 | 6/1985 | Hagase ....................... 525/328.8 |
| 4,632,901 | 12/1986 | Valkirs et al. . |
| 4,654,039 | 3/1987 | Brandt et al. . |
| 4,727,019 | 2/1988 | Valkirs et al. . |
| 4,818,677 | 4/1989 | Hay-Kaufman et al. . |
| 4,877,586 | 10/1989 | Devaney, Jr. et al. . |
| 4,900,663 | 2/1990 | Wie et al. . |
| 4,912,032 | 3/1990 | Hoffman et al. ............... 436/518 |
| 4,916,056 | 4/1990 | Brown, III et al. . |
| 4,920,046 | 4/1990 | McFarland et al. . |
| 5,147,343 | 9/1992 | Kellenberger . |
| 5,147,646 | 9/1992 | Graham ......................... 424/424 |
| 5,262,297 | 11/1993 | Sutton .......................... 436/824 |
| 5,512,176 | 4/1996 | Blair ............................ 210/633 |

FOREIGN PATENT DOCUMENTS

| | | | |
|---|---|---|---|
| 0061154 | 6/1978 | Japan ........................... 210/642 |
| 8604255 | 7/1986 | WIPO ........................... 210/321.87 |

OTHER PUBLICATIONS

Sigma Chemical Company, *Material Safety Date Sheet*, Oct. 15, 1995, pp. 1–4.

Calbiochem Novabiochem, *Product Data Sheet*, Catalog No. 178530 Aquacide IV, undated.

Stockhausen, *Material Safety Data Sheet*, May 12, 1995, pp. 1–2.

Stockhausen, *Data*, Stockhausen's AP Acrylate Series Product Types and Typical Data, pp. 1–8, undated.

*Primary Examiner*—Joseph W. Drodge
*Attorney, Agent, or Firm*—Brinks Hofer Gilson & Lione

[57] ABSTRACT

The hydrogel-forming polymers are used as absorbents for collecting and concentrating solutions. A solution to be concentrated can be contained in a dialysis membrane, with the hydrogel-forming polymer, or mixture thereof, on the outer surface of the membrane. A hydrogel-forming polymer can be added directly to the solution to be concentrated and the resulting concentrate separated from the gel by filtration of decanting. A hydrogel-forming polymer can be placed in a container formed of porous material and the container can be added to the solution to be concentrated and physically removed after concentration has occurred. Hydrogel-forming polymer can be used as a liquid collection in diagnostic membrane assay cartridges.

14 Claims, 1 Drawing Sheet

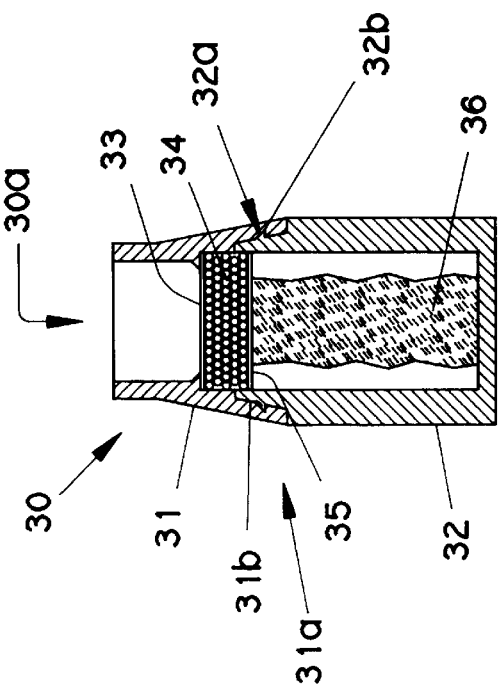
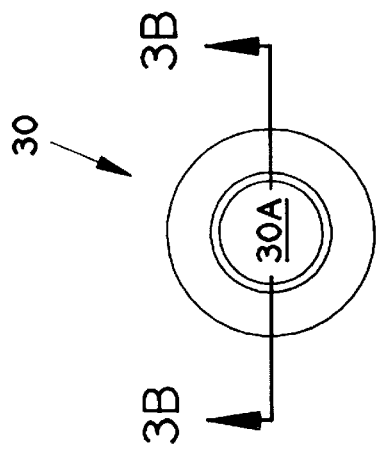
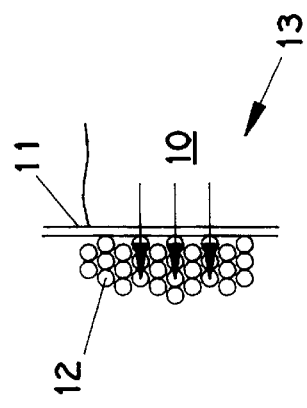
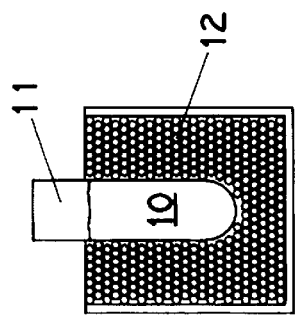
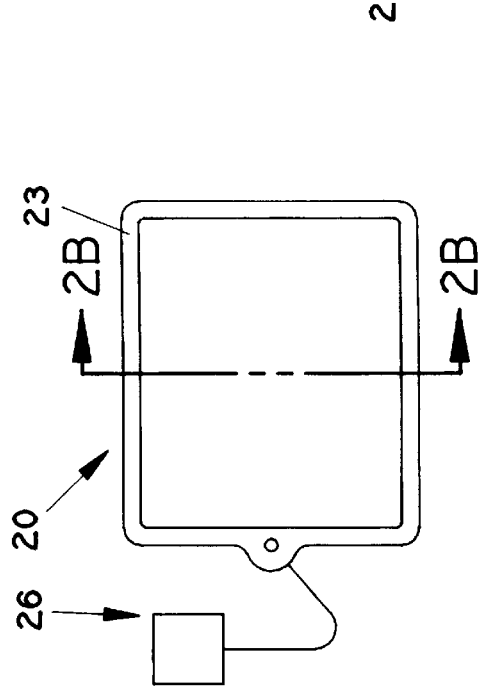

METHODS AND APPARATUS USING HYDROGELS

FIELD OF THE INVENTION

This invention relates to methods and apparatus using hydrogel-forming polymers for concentrating or collecting liquid materials. More particularly, this invention relates to methods and apparatus in which hydrogel-forming polymers assist in the concentration of macromolecule solutions, microparticle suspensions, and in the retention of solutions used in diagnostic and laboratory procedures.

BACKGROUND OF THE INVENTION

The research community, whether situated in an academic or industrial setting, has a continuing need for methods and apparati for concentrating solutions, including particularly solutions of macromolecules or suspensions of microparticles. Current methodologies can lead to contamination of said solutions and can require the use of expensive equipment. In some applications, no satisfactory, easily used and inexpensive method or apparatus currently exists.

For example, to concentrate solutions of macromolecules of interest, it is currently possible to introduce the solution into a bag formed from a semi-permeable membrane (commonly known as dialysis tubing) with pore sizes smaller than the size of the macromolecules(s) of interest. The bag is placed in a container and a water soluble macromolecule, either in powdered form or in a highly concentrated solution, is used to completely surround the bag. These water soluble macromolecules are also larger than the pore size of the semi-permeable membrane to restrict their entry into the bag and subsequent contamination of the contents of the bag. Typical water soluble macromolecules currently used in this procedure include carboxymethylcellulose, available under trade names Aquacide I and Aquacide II from Calbiochem/Novabiochem and polyethylene glycol compound, available from Sigma Chemical Company. When used as a powder, initial wicking of water or buffer from inside the semi-permeable bag dissolves the powder adjacent to the outer surface of the bag. The resulting high concentration of molecules causes the removal of more water or buffer from inside the bag through the Donnan effect. When the water soluble macromolecules are used in the form of a highly concentrated solution, they exert their effect solely through the Donnan effect. In either case, these water soluble macromolecules form a very viscous, honey-like, film or layer on the outside of the bag; a residue which is very hard to remove completely when the bag is opened to recover the now concentrated macromolecules of interest and contamination by the residue is possible.

It is also possible, for example, to concentrate solutions of macromolecules of interest by direct addition of dry polyacrylamide gel. Typical for effecting concentrations by this procedure include Aquacide IV, available from Calbiochem/Novabiochem and polyacrylamide absorbent gel, No. P2433, available from Sigma Chemical Company. As these polyacrylamide gels rehydrate, the openings created within the polyacrylamide gel are smaller than the macromolecules of interest and, thus, size exclusion restricts entry of the macromolecules of interest into the gel, effectively concentrating the macromolecules of interest outside the gel. The concentrated solution of macromolecules of interest is recovered by decanting the concentrated solution of macromolecules from the hydrated gel, or filtering it to remove the hydrated gel. The polyacrylamide gels are expensive to use and slow in performance.

Protein can be concentrated in various containers utilizing a tube open at one end and sealed with a semi-permeable membrane at the other end. The pores of the semi-permeable membrane are smaller than the macromolecules of interest, allowing only water or buffer to pass through the pores. These containers, with the solution of macromolecules of interest in the tube, are placed into a small table-top centrifuge. Upon operation of the centrifuge, centrifugal force causes the water or buffer to pass through the semi-permeable membrane into a receptacle behind the membrane, concentrating the solution of macromolecules of interest remaining in the tube portion of the container. This procedure requires expensive equipment and is applicable only to concentration of small volumes.

To concentrate suspensions of microparticles, two methods currently exist; centrifugation and filtration. Centrifugation requires expensive equipment and cannot be practically applied to microparticles which have approximately the same density as the solution in which they are suspended. Very small microparticles (<100 nm) never settle out because Brownian motion overcomes the centrifugal force generated. Even when centrifugation is practical, it is time-consuming, requiring 30 minutes or more and volumes are limited to the capacity of the centrifuge used. In some cases, the packing of the microparticles caused by centrifuging, causes the microparticles to clump, requiring re-suspension by sonication, which introduces free radicals and intense heat to the suspension which may be undesirable.

Filtration of microparticle suspensions can be accomplished with currently known procedure only if the microparticles are greater than 100 nanometers. No semi-permeable membrane filter device is currently known to be available for particles less than this size. Even for particles greater than 100 nanometers, filtration with these devices can cause undesirable clumping of the microparticles due to the forces generated by filtering at the surface of the semi-permeable membrane.

Methods and apparatus are available for performing solid phase immunoassay procedures, conveniently inside and outside of a clinical laboratory to determine the presence of antibodies or antigens of interest in a sample. Such method and apparatus include, for example, home pregnancy kits. Such methods and apparatus have relied upon the affinity of one member of an antigen-antibody pair to bind with or to the other member of the antigen-antibody pair.

In such method and apparatus, a "capture" member of the antigen-antibody pair of interest is carried by a porous substrate in a cartridge providing containment for one or more samples or solutions used in the procedure. A liquid sample or solution to be tested is then added to the cartridge and passes through the substrate to the containment portion of the cartridge which is generally provided with an opening to allow air to escape as the one or more liquids enter the containment portion. If the liquid sample includes the other member of the antigen-antibody pair of interest, it will become bound with the member carried by the substrate and may be used to develop a visual indication of the result of the procedure, sometimes with the use of subsequent washing and developing liquids.

In practice, cartridges used in such methods and kits have included generally a porous membrane in combination with a mesh and a sponge or pad to absorb and "wick" the liquids from the porous membrane and assist in their containment by the cartridge. The porous membrane has had a portion of its surface treated with an antigen or antibody capable of bonding with an antibody or antigen of interest. Such kits have included solutions for preparing a liquid sample, for washing the membrane, for providing labeled antibody or antigen as appropriate, and for developing a visual indication of the label; in some kits applicators to apply the liquid sample and solutions. Exemplary patents disclosing such immunoassay methods, apparatus and kits include U.S. Pat. Nos.: 3,645,687; 3,843,324; 3,966,897; 4,039,652; 4,061, 468; 4,094,647; 4,125,372; 4,138,474; 4,153,675; 4,168, 116; 4,180,383; 4,193,983; 4,235,601; 4,376,110; 4,424, 279; 4,427,769; 4,486,530; 4,818,677; 4,632,901.

The prior methods and apparatus are not entirely satisfactory. For example, the absorbent sponge or pad used to "wick" liquids away from the porous membrane has limited capability to absorb liquid and can allow a reverse transfer of liquid back to the porous membrane, reducing the ability of the apparatus to provide a predictable and reliable visual indication of the test results. In addition, the limited ability of existing cartridges to absorb and accommodate the liquids used in such procedures increases the likelihood that liquids will escape containment, which is highly undesirable and can inhibit the use of such cartridge for some test procedures.

BRIEF STATEMENT OF THE INVENTION

The invention provides easily used, inexpensive and reliable methods and apparatus for concentrating and collecting liquid solutions and materials.

In this concentration of solutions, for example, a solution to be concentrated can be placed in contact with one side of a semi-permeable membrane (such as a dialysis membrane) and the other side of the semi-permeable membrane can be allowed to contact a hydrogel-forming polymer, or a mixture containing a hydrogel-forming polymer, to provide liquid transfer through the semi-permeable membrane and concentration of the solution. In the invention hydrogel-forming polymer contained within a bag or cartridge formed, at least in part, with a semi-permeable material can be placed in a solution to be concentrated, or the solution to be concentrated can be placed within a container formed, at least in part, with a semi-permeable membrane that is placed in contact with the hydrogel-forming polymer.

In the collection of liquids, for example, a cartridge for conducting an immunoassay procedure can include a hydrogel-forming polymer in contact with a porous membrane carrying a capture member of an antigen/antibody pair of interest to absorb a liquid sample being tested and "wick" it away from the porous membrane and the test reaction and to assist in the containment of the liquid sample, and any additional liquids used in the test, within the cartridge.

Hydrogel-forming polymers used in the invention are materials which are capable of absorbing large quantities of fluids such as water or water solutions. The quantities absorbed can be 200 to 300 times the weight of the hydrogel. Such hydrogels have been described in such U.S. patents as Hayer, et al., U.S. Pat. No. 3,669,103, issued Jun. 13, 1972. Hydrogel-forming polymers are frequently synthesized by polymerizing unsaturated carboxylic acids or derivatives thereof. These polymers are made water insoluble by cross-linking the carboxyl with cross-linking agents such as di- or poly-functional monomers.

BRIEF DESCRIPTION OF THE DRAWINGS

FIG. 1A is a diagrammatic illustration of a means for concentration of a solution with the invention;

FIG. 1B is an enlarged diagram of a portion of FIG. 1A to illustrate transfer of liquid through a porous membrane to a hydrogel-forming polymer;

FIG. 2A is a side view of another means of the invention for the concentration of solutions;

FIG. 2B is a cross-section view of the means of FIG. 2A taken at a plane corresponding line 2B—2B of FIG. 2A;

FIG. 3A is a top view of another means of the invention for collection of liquids in an immunoassay test procedure; and FIG. 3B is a cross-section of the means of FIG. 3A taken at a plane corresponding to line 3B—3B of FIG. 3A;

DETAILED DESCRIPTION OF THE INVENTION

The present invention presents a novel use of hydrogel-forming polymers in the concentration of solutions, particularly solutions including macromolecules or suspensions of microparticles. Typical uses of this material would be in a laboratory or industrial setting where it is necessary to concentrate solutions or suspensions without the use of expensive equipment or, the risk of contamination or other undesirable collateral effects such as heat. In addition, the invention presents the novel use of hydrogel-forming polymers in cartridges used for diagnostic assays.

The present invention allows for the concentration of macromolecules in solution or microparticles in suspension with or without the use of a semi-permeable membrane. When a semi-permeable membrane is employed, it is anticipated that the pore size of the semi-permeable membrane chosen for a particular application will be at least smaller than the macromolecule or microparticles of interest, to serve simply as a barrier between the macromolecules or microparticles to be concentrated and the surface of the hydrogel-forming polymer.

As demonstrated in the following examples, it is possible to concentrate solutions of macromolecules and suspensions of microparticles by the direct addition of the hydrogel-forming polymer contained in porous gel filter material; therefore, any filter material with a size retention greater than the smallest diameter of the dry hydrogel-forming polymer used, can readily be employed in the invention in place of a semi-permeable membrane. When a semi-permeable membrane or porous gel filter material is used, it will preferably be, it is believed in the form of a bag.

In the invention, as illustrated by FIGS. 1A and 1B, solution, or suspension to be concentrated 10, may be introduced into a bag 11 formed of a liquid permeable material that can contain the solution or suspension. Hydrogel-forming polymer 12 is placed in contact with the outside surface of the bag to effect the transfer of liquid through the material of the bag 11, as illustrated by arrow 13 of FIG. 1B, thus concentrating the solution or suspension remaining within the bag. The desired concentration of the solution can be effected by controlling the time of exposure of the bag to the hydrogel-forming polymer.

In the past, macromolecules such as carboxymethylcellulose and polyethylene glycol compound have been used for the concentration of macromolecule solutions held within dialysis tubing (pore sizes typically expressed as 100 Daltons to 50,000 Daltons). In such prior procedures, the soluble macromolecule compounds leave a viscous residue, not readily removed from the outside surface of the dialysis tubing, which can contaminate the solution of interest. The present invention is an improvement to the state of the art in that the hydrogel-forming polymer does not dissolve in the process of removing liquid from inside dialysis tubing and rinses off easily from the outside of the bag, eliminating the risk of contamination. In addition, concentration of microparticle suspensions is not effected by any such current method, and semi-permeable membranes or filter materials with pore sizes greater than 50,000 Daltons are not currently utilized in any such process.

The present invention can also be used to effect the concentration of macromolecules or microparticles through the process of introducing, preferably, a hydrogel-forming polymer or mixture thereof, into container, a bag, preferably made of semi-permeable membrane, or a porous gel filter material, which can be any porous filter material that will prevent the transfer of the smallest particles of the hydrogel-forming polymer, and placing the container or bag into the solution or suspension to be concentrated. This procedure can be likened to the use of a tea bag to make tea by introducing it into water and removing it easily from the water once tea is made. In the procedure of the invention, however, after the container of hydrogel-forming polymer, which is novel, is added to a solution to be concentrated, liquid is absorbed by the hydrogel-forming polymer, thereby concentrating the solution, and the absorbed liquid is easily lifted from the concentrated solution with removal of the container.

FIGS. 2A and 2B illustrate a solution concentration means usable in this procedure. As shown in FIGS. 2A and 2B, a preferable container 20 is a bag formed by two small sheets of porous filter paper 21, 22 bound at their edges 23 to form a bag-like container 20. The porous filter material from which the sheets 21 and 22 are made need only have a pore size sufficient to contain the smallest particle of liquid absorbent (24 in FIG. 2B) within the bag, for example, tea bag material. If desired, one or both sheets 21 and 22 can be formed with pleats to permit the container 20 to expand as a hydrogel-forming polymer absorbs liquid. If desired, the container 20 can be provided with an attached string 25, or other means to assist in its removal from the solution being concentrated. As is readily apparent, however, no such container removal means is necessary since the concentrated solution can be decanted to separate the absorbed liquids, which will be retained with the hydrogel within the container. In addition, the container and absorbed liquid can be removed from the solution with an implement such as a common spoon.

The solution concentrating means of FIGS. 2A and 2B and the method of its use in laboratory use is novel. A hydrogel-forming polymer is greatly preferred as the contained liquid absorbent because of the quantity of liquid it can absorb, the speed of its absorbance and its low cost. For example, while a polyacrylamide gel may be used in such a container to concentrate solutions of macromolecules, polyacrylamide gel is expensive and relatively slow in accomplishing this task and is not preferred (as shown in the examples below).

The present invention also relates to the use of a hydrogel-forming polymer as a component in immunoassay cartridge devices to absorb and retain liquids which pass through the specialized membrane which serves as the focal point of the reactions underlying the assay.

FIGS. 3A and 3B illustrate one embodiment of an immunoassay cartridge of the invention. As shown in FIG. 3B, such a cartridge 30 can be formed by two molded plastic outer shells, an upper shell 31 and a lower shell 32. For convenience in assembly, the lower skirt portion 31a of the lower shell 31 is formed with an annular groove 31b on its inner surface, and the lower shell 32 is formed with a mouth-forming portion 32a including an annular protuberance 32b so that the upper and lower shells can be snapped together as an assembly with protuberance 32b and groove 31b engaging to fasten the cartridge shells 31 and 32 together. In such cartridges, a porous membrane substrate 33 is retained under the opening 30a of the cartridge 30. The porous membrane 33 frequently carries one member of an antigen/antibody pair of interest which is exposed to a liquid sample, and other liquids poured into the opening 30a of the cartridge. In the invention, a hydrogel-forming polymer 34 is retained in contact with the lower surface of the porous membrane 33, for example, by another porous supporting substrate 35. The hydrogel-forming polymer 34 absorbs and traps liquids that pass through the porous substrate 33 and prevents their reverse flow to the porous substrate 33. The lower shell 32 of the cartridge 33 can also carry collapsible sponge or cellular foam member 36 which can support the hydrogel-forming polymer against the porous membrane 33 and allow its expansion as it absorbs liquid.

Hydrogel-forming polymer can absorb a greater volume of liquid when confined to the same physical volume than the porous wicking material currently being used. Hydrogel-forming polymers are also better at preventing the back flow of liquid to the porous membrane 33, than the current porous wicking material. This backflow to the specialized membrane causes increases in the background staining of the porous membrane, resulting in less certainty in the interpretation of the visual results of the assay.

This use of hydrogel-forming polymer is novel. In the embodiment, the hydrogel powder 34 is supported by a porous plastic disc 35, which is in turn supported by a water soluble starch plug 36. This embodiment maintains a tight seal between the porous membrane 33 and the top of the cartridge device, while providing the space required for the expansion of the hydrogel-forming polymer as the liquids are introduced onto the opening 30a of the cartridge. This choice of water soluble starch plug should not be construed as the only way to effect the dual purpose of support and expansion volume. Such a cartridge embodiment can be used with a number of tests, including tests which use a plurality of liquid to wash and develop a visual test results because among other reasons, the hydrogel-forming polymer can absorb up to 200 times its weight in liquid.

In practicing the invention, a preferred hydrogel-forming polymer is:

1. Chemical basis: sodium salt of cross-linked polyacrylic acid; polyacrylate/polyalcohol copolymers; or polyacrylamide and acrylamide potassium acrylate copolymer.

2. Particle size: 1–850 microns.

3. Specific gravity: 400–700 g/l.

4. Moisture content: 0–6%

5. pH Value: 5–8(1% gel in 0.9% NaCl).

Particularly useful hydrogel-forming polymers that are sold by Stockhausen, Inc. of Greensboro, N.C. as under its designation AP 85-13, or FAVOR™ SXM-75 which has a particle size range of 100–850 microns, a moisture content of 0.2% (2% maximum) and a pH of 6.0,±0.5 pH.

Using Hydrogel or a Mixture of Hydrogel to Remove Liquid from a Solution Contained in Dialysis Tubing Example 1

50 ml of distilled water, tinted blue with food coloring, was placed in approximately 14 inches of dialysis tubing (Sigma Chemical Company part No. D-9777). The filled dialysis tubing was placed in 80 g of hydrogel-forming polymer (Favor SXM-75), in a manner to ensure complete surface coverage. After three hours exposure to the hydrogel-forming polymer, the amount of fluid in the dialysis tubing had shrunk from a height of 22.5 cm to 15 cm. After 21 hours exposure to the hydrogel-forming polymer, all of the liquid inside the dialysis tubing had been absorbed.

Using a Mixture of Hydrogel and a Wicking Material to Absorb Liquid

Example 2

A mixture of 50 percent polyethylene glycol and 50 percent hydrogel (Favor SXM-75) was used to cover 7 cm of dialysis tubing filled with distilled water dyed blue with food coloring. After one hour, the height of water in the dialysis tubing had decreased from 7 cm to 5.5 cm.

In both Example 1 and Example 2, the hydrogel and remaining polymer were easily rinsed from the outer surface of the dialysis tubing. Although only colored water was used in Examples 1 and 2, the results would have been unchanged if there had been particulate matter, such as macromolecules or micro particles, in the solution to be concentrated.

Materials presently used to concentrate solutions held within dialysis tubing, such as carboxymethylcellulose and polyethylene glycol compound, form viscous, honey-like films on the outer surface of the membrane. These films are difficult to remove completely by rinsing. This film can easily contaminate the concentrated solution as it is removed from the dialysis tubing. The hydrogel polymer rinses quickly and completely, leaving virtually no residue.

To Concentrate Solutions and Suspensions by Adding Hydrogel Directly to the Solution or Suspension Example 3

To 2 ml of solution consisting of 1 mg/ml of bovine serum albumin in 0.9 percent sodium chloride, was added 40 mg of hydrogel-forming polymer (Favor SXM-75). After two minutes, the concentrated solution was filtered off and assayed for protein concentration. The following results were obtained:

|  | Before concentrating | After concentrating |
| --- | --- | --- |
| Protein Concentration | 1.00 mg/ml | 1.24 mg/ml |

Example 4

The experiment in Example 1 was repeated using 2 mg/ml of bovine serum in 0.9 percent sodium chloride. Again, 40 mg of hydrogel-forming polymer (Favor SXM-75) was added to a 2 ml solution. After two minutes, the concentrated solution was filtered and assayed for protein. The following results were obtained:

|  | Before concentrating | After concentrating |
| --- | --- | --- |
| Protein Concentration | 2.00 mg/ml | 2.68 mg/ml |

For protein concentration, other materials commercially available, such as Aquacide IV from Calbiochem/Novabiochem, are much slower in absorbing liquid, cost ten times as much, and, in the latter case, absorb much less liquid than Favor SXM-75 hydrogel-forming polymer. The time required by Favor SXM-75 hydrogel-forming polymer, polyacrylamide and by Aquacide IV to absorb ten times their weight in deionized water was respectively 4 sec., 59 sec., and more than 1 hour. Even with an overnight incubation of Aquacide IV, it would not absorb 100 times its weight in deionized water. Favor SXM-75 took 87 sec. to absorb 200 times its weight in deionized water, and polyacrylamide absorbent gel took 41 minutes to absorb this much.

Example 5

To 20 ml of an 0.5 percent suspension of latex particles (diameter 175 nanometers) was added 40 mg of hydrogel-forming polymer (Favor SXM-75). This was mixed for 10 minutes by mild agitation. The suspension was filtered through a #588 pre-pleated Schleicher & Schuell filter set into a funnel. Nine ml of filtrate was obtained. A sample of the original 0.5 percent latex suspension and a sample of the filtrate was diluted 1:40 with distilled water and the absorbance of the dilutions was measured at 650 nm. The following data were obtained:

|  | Original suspension | Filtrate |
| --- | --- | --- |
| Absorbance 1:40 dilution at 650 nm | 0.203 | 0.365 |

These data show that the hydrogel-forming polymer concentrated the latex suspension 1.8 fold.

The only other practical procedure for concentrating microparticles is to use high speed centrifugation. This requires the use of an expensive piece of equipment, takes 30 minutes to several hours and is not applicable to particles which are small enough for Brownian motion to counter the centrifugal force. The hydrogel-forming polymer can rapidly concentrate the microparticles, with no capital equipment and great time savings.

Hydrogel-Forming Polymer Contained in a Container Used to Concentrate a Solution Example 6

A semi-permeable membrane bag 3 cm by 5 cm was made from Gelman Supor-100 semi-permeable membrane having a pore size of 0.1 um. The bag contained 0.258 g of hydrogel-forming polymer (Favor SXM-75). The bag and contents were placed in a 20 ml solution of 0.5 percent latex particles (175 nanometer diameter). After one hour and 20 minutes, the amount of liquid was reduced to 9 ml. After 19.5 hours, the amount of liquid was reduced to 1 ml. A spectroscopic measurements at 650 nm on a 1:10 dilution of pre and post concentrated solutions gave the following results:

|  | Pre-concentration | Post-concentration |
| --- | --- | --- |
| Absorbance at 650 nm | 0.025 | 0.120 |

This shows an apparent increase in latex concentration of 5 fold.

No similar type of solution concentrating means which incorporates a semi-porous membrane as a "bag" to contain a liquid absorbing substance of any kind is known. The advantage of using a liquid absorbent in a porous membrane as opposed to pouring directly into a solution is that it:

1) Allows for the easy removal of the liquid absorbent and the absorbed liquid from the concentrated solution.

2) The pore size of the semi-permeable membrane limits the size of the solute that can be absorbed by liquid absorbent.

3) The charges of the surface of the membrane can be varied (by varying the membrane), thus attracting or repelling solutes in solution.

Using Hydrogel to Trap Moisture In Diagnostic Membrane Assay Kits

Example 7

A commercially available diagnostic cartridge (Hybritech ICON™ II HCG (Urine)) having approximate dimensions of 4 cm tall and 3 cm in diameter, was separated into its 2 outer shells. The interior components consist of an upper membrane, a thin piece of filter paper, a plastic porous disk, approximately 2 mm thick, and a moisture absorbing plug approximately 2.6 cm in diameter and 2.3 cm tall.

In our experiment, the moisture absorbing plug was removed and 0.25 g of hydrogel (Favor SXM-75) was sandwiched between two plastic porous disks. This sandwich was supported by a soluble starch plug 1 cm in diameter and 1.75 cm tall (Bio-8, from Free-Flow Packaging).

The bottom of the outer shell had two holes placed near the bottom to allow air to escape.

This modified cartridge was run in parallel with an unmodified Hybritech ICON™ II HCG (Urine) cartridge following the package insert directions. When the parallel tests were conducted in accordance with Hybritech's directions, equivalent results were obtained in each test, establishing that the use of the hydrogel-forming polymer will not interfere with the reliability of a diagnostic cartridge. As indicated above, sample and liquid containment will be improved with a cartridge of the invention.

At the present time, moisture is trapped within membrane cartridges by absorbent paper or porous plastic material. The limitation of this existing configuration is that it limits the amount of volume that can be trapped to the physical dimensions of the absorbing medium. A hydrogel-forming polymer, on the other hand, can expand as it is absorbing the solution to many times its original size and thus greatly increasing the amount of fluid that can be used in the assay.

For example, the porous plug used to capture liquid in the ICON II cartridge has a physical volume of 16.6 cc and will absorb 12.6 cc of liquid; 75.9 percent of its physical volume. Favor SXM-75, if confined to the same space, would absorb 16.55 cc of deionized water, 16.27 cc of 0.9 percent saline solution, or 15.94 cc of 0.5 M saline solution; representing an increase of 31.3 percent, 29.1 percent and 26.5 percent capacity over the existing material.

We claim:

1. A method of concentrating a solution, comprising
    contacting the solution with one side of a porous gel barrier material and contacting the other side of the porous gel barrier material with a substance including a water-insoluble hydrogel forming polymer, and
    allowing liquid to pass through the porous gel barrier material to concentrate the solution.

2. The method of claim 1 wherein the other side of the porous gel barrier is concentrated with a mixture including said water-insoluble hydrogel-forming polymer.

3. A method of obtaining a desired concentration of a suspension including particulates and a solution, comprising
    placing a water-insoluble hydrogel-forming polymer in contact with the suspension and allowing the hydrogel-forming polymer to absorb the solution until the desired concentration is obtained, and
    separating the hydrogel-forming polymer and absorbed solution from the desired concentration of solution and particulates to provide the desired concentration of the suspension for further use.

4. A method of concentrating a solution or suspension, comprising
    placing a water-insoluble hydrogel-forming polymer in a container formed from a porous gel barrier material,
    placing the container of water-insoluble hydrogel-forming polymer into the solution,
    allowing liquid to pass through the porous gel barrier material for absorption by the water-insoluble hydrogel-forming polymer to concentrate the solution or suspension, and removing the container of water-insoluble hydrogel-forming polymer and absorbed liquid from the container of concentrated solution or suspension.

5. The method of claim 4 wherein an appendage is attached to the container to facilitate its removal.

6. The method of claim 4 wherein the porous gel barrier material is formed to provide an expandable container.

7. The method of claim 4 wherein the container has a solution or suspension contacting surface with an area in the range of about 0.1 to about 10.0 $cm^2$/ml of solution.

8. The method of claim 7 wherein the solution contacting area of the container is about 1.5 $cm^2$/ml of solution.

9. The method of claim 4 wherein the container comprises a bag-like container formed from a fibrous material having a pore size small enough to contain particulate matter as small as one micron, and the water-insoluble hydrogel-forming polymer is contained within the bag-like container.

10. A method of concentrating a suspension containing particulates and a solution, comprising
    placing the suspension to be concentrated into a container formed with a semi-permeable membrane having pores smaller than the particulates,
    placing the container in contact with a water-insoluble hydrogel-forming polymer for a time sufficient to allow solution to be absorbed by the water-insoluble hydrogel-forming polymer thereby concentrating the suspension.

11. A method of concentrating a solute-containing solution by direct addition of a water-insoluble hydrogel-forming polymer to the solution to be concentrated and subsequent removal of the water insoluble hydrogel-forming polymer from the concentrated solution upon obtaining a desired concentration so that the concentrated solution is available for further use.

12. A method of concentrating a suspension by direct addition of a water-insoluble hydrogel-forming polymer to the suspension to be concentrated, and subsequent removal of the water insoluble hydrogel-forming polymer from the concentrated suspension upon obtaining a desired concentration so that the concentrated solution is available for further use.

13. In a cartridge for conducting immunoassay procedures including a porous membrane carrying a member of an antigen/antibody pair of interest and providing a test detection site and means for absorbing from the porous membrane a liquid sample to be tested for the other member of the antigen/antibody pair of interest, the improvement comprising a water-insoluble hydrogel-forming polymer supported in contact with the porous membrane and providing said means to absorb said liquid sample from the porous membrane.

14. The cartridge of claim 13 wherein the hydrogel-forming polymer is supported in contact with the porous membrane by a collapsible support contained within a lower portion of the cartridge.

* * * * *